United States Patent

Adrian et al.

[11] Patent Number: 5,423,797
[45] Date of Patent: Jun. 13, 1995

[54] ACOUSTIC CATHETER WITH ROTARY DRIVE

[75] Inventors: Sorin Adrian, Penn Valley; Peter A. Lewin, Wyndmoor; Sorin Siegler, Merion; Paul Walinsky, Wyndmoor; Richard C. Hayes, Penn Valley, all of Pa.

[73] Assignee: Medelex, Inc., Penn Valley, Pa.

[21] Appl. No.: 232,687

[22] Filed: Apr. 25, 1994

[51] Int. Cl.⁶ .............................................. A61B 17/00
[52] U.S. Cl. ......................................... 606/1; 604/22
[58] Field of Search ................ 604/22; 601/2; 607/97; 606/1, 169, 171

[56] References Cited

U.S. PATENT DOCUMENTS

| | | | |
|---|---|---|---|
| 3,433,226 | 3/1969 | Boyd | 606/169 X |
| 5,156,143 | 10/1992 | Bocquet et al. | 604/22 X |
| 5,211,646 | 5/1993 | Alperovich et al. | 606/169 X |
| 5,243,992 | 9/1993 | Uflacker et al. | 604/22 X |
| 5,305,731 | 4/1994 | Bucholtz | 601/2 X |
| 5,326,342 | 7/1994 | Pflueger et al. | 604/22 |

*Primary Examiner*—Peter A. Aschenbrenner
*Attorney, Agent, or Firm*—William H. Meise

[57] ABSTRACT

An acoustic catheter reduces transmission losses and unwanted heating of the transmission member by driving the catheter a rotary motor. The catheter includes an elongated body and a shaft extending longitudinally therethrough. The shaft is adapted for coupling to a rotary motor. A rotary-to-axial motion converter is coupled to the shaft at distal end of the catheter, for converting rotary shaft motion into axial acoustic motion. In one embodiment, the rotary-to-axial motion converter includes a swash plate driven by the shaft. The swash plate defines a surface which, at an angularly fixed reference point, moves axially in response to the rotary motion of the swash plate. A follower bears on the swash plate, for moving axially in response to axial motion of the follower. The follower includes a projection bearing on the swash plate and a spring urging the follower toward the swash plate. In one embodiment, the swash plate has a sinusoidal surface, while another embodiment has notches cut into the surface. The follower generates acoustic energy within a fluid medium, and may have a concave fluid coupling surface. To aspirate the material removed from arterial walls, one or more lumens extend through the catheter. In a particular embodiment of the invention, the rotary shaft is hollow, in order to allow a guide wire to pass therethrough.

12 Claims, 5 Drawing Sheets

ACOUSTIC CATHETER WITH ROTARY DRIVE

FIELD OF THE INVENTION

This invention relates to medical catheters, and more particularly to catheters for ablation, angioplasty, and/or other medical procedures using acoustic energy or ultrasound, in which the acoustic energy is derived from a rotary shaft.

BACKGROUND OF THE INVENTION

Several hundred thousand people die in the United States each year from acute myocardial infarction, and many more suffer from chronic heart problems. A major contributing factor in both acute and chronic heart problems is a reduction in nutrient blood flow to the muscles of the heart resulting from a reduction of blood flow through the coronary blood vessels. The reduction in flow may be caused by deposits of atherosclerotic plaque on the walls of the blood vessel, which causes a narrowing of the lumen or channel of the blood vessel. When the lumen is sufficiently narrowed, the rate of flow of blood may be so diminished that spontaneous formation of a thrombus or clot occurs by a variety of physiologic mechanisms. As is known, once a blood clot has started to develop, it extends within minutes into the surrounding blood, in part because the proteolytic action of thrombin acts on prothrombin normally present, tending to split this into additional thrombin which causes additional clotting. Thus, the presence of atherosclerotic plaque not only reduces the blood flow to the heart muscle which it nourishes, but is a major predisposing factor in coronary thrombosis.

Among the treatments available for the conditions resulting from plaque formations are pharmacological means such as the use of drugs, for example nitroglycerin, for dilating the coronary blood vessels to improve flow. In those cases too far advanced to be manageable by drugs, surgical treatment may be indicated. One of the surgical techniques commonly used is the coronary bypass, in which a substitute blood vessel shunts or bypasses blood around the blockage. The bypass operation is effective, but is expensive and subject to substantial risks.

Another treatment for plaque formations is mechanical removal by means of a rotary cutter catheter, as described, for example, in U.S. Pat. Nos. 4,445,509 and 4,990,134, issued May 1, 1984 and Feb. 5, 1991, respectively, both in the name of Auth. Catheters are known in which a cutter can be driven at speeds as great as 200,000 rpm. When the cutter is applied to the arterial walls, the walls may undesirably be perforated.

Percutaneous transluminal balloon coronary angioplasty is a widely used alternative to open-heart coronary bypass surgery for the treatment of acute and chronic heart problems. This method involves insertion of a deflated balloon into the lumen of an artery partially obstructed by plaque, and inflation of the balloon in order to enlarge the lumen. The lumen remains expanded after removal of the catheter, but the obstructing material remains. Among the problems with this technique, as described in the article "Ultrasonic Plaque Ablation," by Siegel et al., published at pp 1443–1447 of Vol. 78, No. 6, December 1988 issue of the periodical Circulation, are those involved in introducing the catheter with its balloon into a blood vessel which is completely or almost completely occluded, and restenosis of the narrowed vessel after the angioplasty procedure by recurrence of the arterial plaque.

Microwave aided balloon angioplasty is described in U.S. Pat. No. 4,643,186 issued Feb. 17, 1987 in the name of Rosen et al. In the arrangement as described by Rosen et al., a catheter including a microwave transmission line terminates at its distal end in an antenna surrounded by a balloon. During angioplasty, microwave power is applied to the proximal end of the catheter and flows to the antenna, which radiates the energy to the plaque for heating and thereby softening the plaque. The balloon is expanded against the softened plaque to thereby expand the lumen of the blood vessel. While microwave heating improves balloon angioplasty, the plaque is not removed by the angioplasty, and may expand after the procedure, or if it does not expand, may provide a base upon which additional plaque may be deposited.

Another technique which has recently received a good deal of attention is transluminal laser catheter angioplasty. This treatment involves introduction into the coronary artery of a fiber optic cable, the proximal end of which is connected to a laser energy source. The distal end of the fiber optic cable is directed towards the plaque. The laser is pulsed, and the resulting high energy light pulse vaporizes a portion of the plaque. Many problems remain unsolved in laser catheter angioplasty, as in mechanical cutting catheters. When the energy of the laser discharge is directed towards the arterial walls, the walls may undesirably be perforated. Further problems relate to the difficulty in matching the characteristic of lasers and fiber optic cables to the frequency absorption characteristics of various types of plaque, and the by-products of the destruction of the plaque.

Experimental studies have shown that ultrasound or acoustic angioplasty has the potential for differentiating between normal arterial walls and abnormal walls including atherosclerotic plaques and thrombi, as described, for example, in "Experimental Ultrasonic Angioplasty:Disruption of Atherosclerotic Plaques and Thrombi in Vitro and Arterial Recanalization in Vivo," by Rosenschein et al., published at pp 711–717 of Vol. 15, Mar. 1, 1990 issue of the J. Am. Coll. Cardiology, and in "Ability of High-Intensity Ultrasound to Ablate Human Atherosclerotic Plaques and Minimize Debris Size," by Ernst et al., published at pp 242–246 of Vol. 68 of The American Journal of Cardiology, Jul. 15, 1991. It appears that significant ultrasonic energy must be applied to the plaque in order to effect its removal. U.S. Pat. No. 3,565,062, issued Feb. 23, 1971 in the name of Kuris, describes an ultrasonic catheter including an electrodynamic, piezoelectric or magnetostrictive ultrasonic motor operating in the range of 1000 Hz to 100 KHz, which may also be operated in a swept-frequency mode. The vibrations from the motor are coupled, through an elongated transmission member which extends through the catheter, to a vibrating tool or head, shaped for removal of plaque. As described therein, when the device is operated at a fixed frequency, nodes along the transmission member are heated. U.S. Pat. No. 5,163,421, issued Nov. 17, 1992 in the name of Bernstein et al. describes the problem of heating of the transmission member, and reduction of the power transmitted to the tool due to transmission losses in the transmission member. The solution suggested in the Bernstein et al. patent is the use of a high Q material. However, even with the use of high-Q transmission members, losses in the vicinity of 50% (−3 dB) occur in ultrasonic catheters of the lengths necessary for coronary angioplasty, and these losses increases significantly at bends in the transmission member.

Improved angioplasty catheters are desired.

SUMMARY OF THE INVENTION

An ultrasound or acoustic angioplasty catheter according to the invention reduces transmission losses, and reduces unwanted heating of the transmission member, by adapting the catheter to be driven by a rotary motor, and by generating the acoustic energy with the body, rather than, as in the prior art, generating the acoustic energy without or outside the body and coupling it into the body by means of a transmission member such as a longitudinally excited wire. A catheter according to the invention includes an elongated body defining a distal end and a proximal end, and a shaft extending longitudinally through the body. The shaft includes a drive coupling arrangement near the proximal end of the catheter, which is adapted to be coupled to the rotary motor, for causing the shaft to be driven in a continuous-rotation manner. A rotary-to-axial motion converter is coupled to the shaft near the distal end of the catheter, for converting the rotary motion into axial motion in the form of acoustic energy. In a particularly advantageous embodiment of the invention, the rotary-to-axial motion converter includes a swash plate coupled to the shaft for being rotationally driven thereby. The swash plate defines a surface which, at a reference point which is angularly fixed relative to the catheter body, moves axially in response to the rotary motion of the swash plate. A follower is coupled to the swash plate and bears on the surface of the swash plate, for moving axially in response to axial motion of the follower surface. The follower may include a projecting portion bearing on the swash plate and a spring bearing on the follower and the catheter body, for urging the follower toward the swash plate. In one embodiment, the swash plate has a sinusoidal surface, for generating a single acoustic tone, while another embodiment has notches cut into the surface of the swash plate, to generate a fundamental tone and harmonics. The follower generates the acoustic energy within a fluid medium such as blood or a clear medium, and possibly within a solid medium, or in a combination of fluid and solid media, and may have a coupling surface or distal surface which is concave, for shaping the distribution of the acoustic energy. In order to aspirate the particles of material dislodged or removed from the arterial walls, the catheter defines one or more open paths or lumens extending from a distal portion of the catheter to a proximal portion of the catheter. At the proximal end of the aspiration lumen, a coupler allows connection to an aspirator, and at the distal end, the aspiration path may be completed by a path or bore extending through the acoustic follower. One or more additional lumens may be provided for allowing introduction of a fluid, for medically indicated purposes. The follower mass is minimized, and maximum energy is thereby coupled to the fluid or solid medium being treated, by making the follower from a low density, high strength material such as carbon-reinforced resin. In a particular embodiment of the invention, the rotary shaft is hollow, in order to allow a guide wire to pass therethrough.

DESCRIPTION OF THE INVENTION

Figure 1:
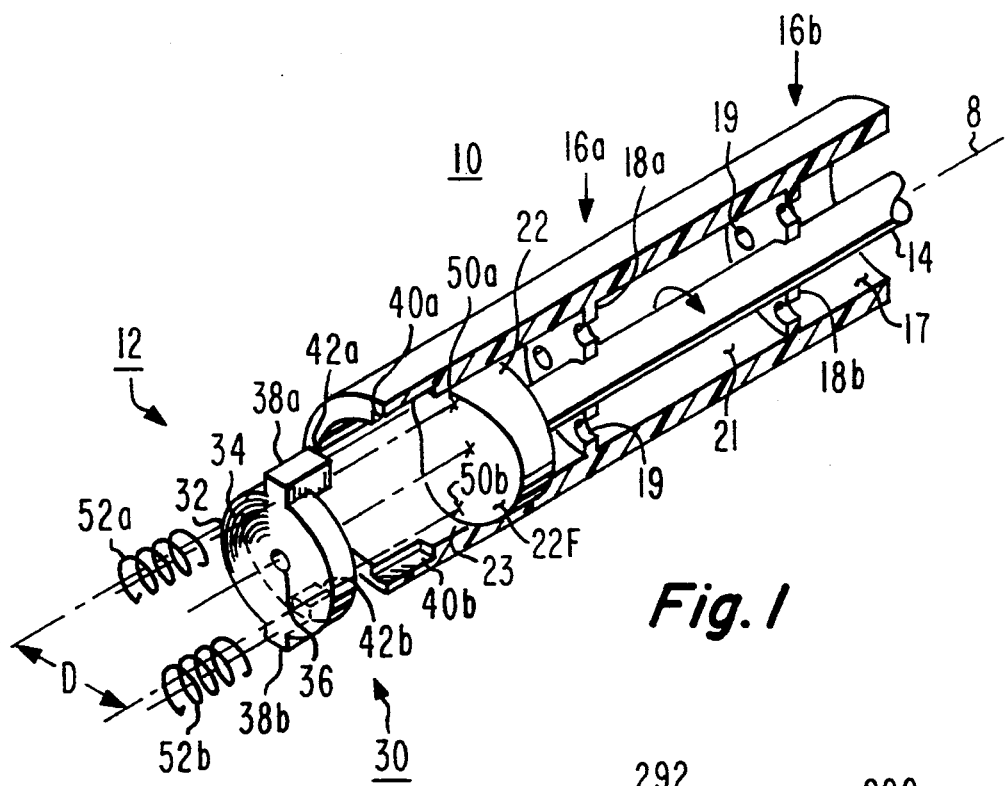
FIG. 1 is a simplified perspective or isometric view, partially cut away to illustrate interior details, of the distal end of a catheter according to an aspect of the invention, illustrating a rotary shaft and a rotary-to-axial-motion converter including a swash plate and an acoustic head.

In FIG. 1, the distal end 12 of a catheter 10 illustrates a flexible rotary shaft capable of continuous rotation, which is adapted to be driven from a proximal end (not illustrated in FIG. 1). Shaft 14 is supported about a common axis 8 at support locations 16a, 16b, along its length by bearing surfaces (not separately designated) in fenestrated bulkheads designated 18a and 18b, respectively. Some of the fenestrations are designated 19. Bulkheads 18a and 18b may be formed integrally with a flexible catheter body 20, thereby defining a longitudinal lumen 17, which may be used for aspiration, as described below, or which may be used for infusing medication or dye. A swash plate 22 in the general form of a circular disk or plate has its "rear" or proximal surface coupled coaxially to the distal end of shaft 14 for being driven thereby in a rotary motion. The "front" or distal surface 22F of swash plate 22 is "wavy", in that the front-to-back thickness of plate 22 varies about its periphery. As illustrated in FIG. 1, the variation in thickness is sinusoidal, with two smooth peaks separated by two smooth valleys. The outer periphery of swash plate 22 is spaced apart by a gap 23 from the inner surface 21 of catheter wall 20, to thereby define a channel or through which fluid may flow during aspiration. Aspiration suction applied to the proximal end (not illustrated in FIG. 1) of lumen 17 results in the flow of fluids through lumen 17.

Those skilled in the art will recognize that, since catheter 10 and shaft 14 of FIG. 1 are flexible, that common axis 8 will, at any particular location, be coaxial with only adjacent portions of the catheter, and that remote portions of the catheter may have axis 8 lying relatively at skew angles.

Also visible in FIG. 1 is a follower designated generally as 30, which coacts with swash plate 22 to form a rotary-to-axial motion converter. Follower 30 includes a generally circular plate-like structure coaxial with common axis 8. Follower 30 has an outer periphery 32 which defines a diameter D which fits closely within the body 20 of catheter 10, but not so closely as to restrain axial motion. Follower 30 defines a conical or funnel-shaped front or distal surface 34 to "focus" the acoustic energy generated by the catheter, and also defines a bore 36 extending from front surface 34 through to the rear surface of follower 30, to allow the aspiration of fluids from the region being treated with acoustic energy. Follower 30 further defines two ribs, ridges or protrusions 38a and 38b, which are diametrically opposite to each other relative to common axis 8. Ribs 38a and 38b extend to a greater diameter than diameter D, and, when follower 30 is assembled into the distal end of catheter body 20, protrude into correspondingly shaped channels or grooves 40a and 40b, respectively, for preventing rotary motion of follower 30, and for allowing a small amount of axial motion. Ribs 38a and 38b also include "leg" portions 42a and 42b, respectively, which extend proximally or "to the rear" of the circular plate-like structure of follower 30, so that, when follower 30 is assembled into the distal end of catheter body 20, legs 42a and 42b of the ribs bear against diametrically opposed portions, designated 50a and 50b, respectively, of front surface 22F of swash plate 22. It may be desirable to provide the legs with low-friction contacts, such as rollers or a TEFLON surface, at the points at which they contact the swash plate. A pair of springs, illustrated as 52a and 52b, bear against follower 30 at rib 38a and 38b, respectively, to urge the follower legs against the swash plate. Springs 52a and 52b are held in place, and bear against, a portion of body 20 of catheter 10 which is not illustrated.

In operation of the arrangement of FIG. 1, catheter 10 is introduced into a vas or blood vessel of a patient to be treated, whereby the distal face 34 of follower 30 is adjacent the treatment site, and is surrounded by liquid such as blood, or by a transparent liquid if the catheter includes a fiber optic scope. Shaft 14 is rotated at a high speed, for example 200,000 rotations per minute (RPM), and swash plate 22 rotates accordingly. With each rotation of the swash plate, a given leg, such as leg 42a, will make two front-to-back excursions, because it goes from a peak of swash plate front surface 22F into the adjacent valley, to the other peak, and a valley back to the first peak. The legs are located so that they contact the swash plate at corresponding, diametrically opposed locations, so that they move forward and aft together. Follower 30 moves fore-and-aft in concert with legs 42a and 42b. A rotational speed of 200,000 RPM corresponds to 3333 rotations per second, which in turn results in 6666 front-to-rear excursions of the follower, or 6666 Hz, well within the acoustic range. The magnitude of the motion is determined by the peak-to-valley depth of the front surface 22F of the swash plate, which, depending upon the desired acoustic pressure, may range from about 10 microns to 500 microns, although special conditions may require excursions outside this range. The front-to-rear excursions of follower 30 couple acoustic energy into the surrounding medium, which will most commonly be liquid, and to such tissue or unwanted deposits as may be contacted. The follower is applied to the region to be treated in a manner similar to that known, for ablating or cutting atherosclerotic plaque or other material with the aid of the acoustic energy generated by the follower.

Also during operation of the arrangement of FIG. 1, the acoustic energy will dislodge or comminute matter, which may be removed by applying aspirating suction to the proximal end of catheter 10. The aspirating suction will be communicated through fenestrations 19 in bulkheads 18a, 18b, . . . , through gap 23 between the outer edge of swash plate 22 and the inner surface 21 of catheter body 20, and through bore 36 in follower 30. The aspirating suction will result in a flow of fluid including the dislodged matter, which prevents it from circulating through the body of the patient.

A principal advantage of the arrangement, as described in conjunction with FIG. 1, is that little power is lost or dissipated in the coupling medium (the rotary shaft) by comparison with the prior art acoustic arrangement, in which the acoustic energy itself is generated outside the body, and is transmitted longitudinally through the transmission member. As a result of using a rotary coupler instead of a longitudinal acoustic coupler, heating at nodes is avoided, so there is no need to reduce the applied power or to sweep the acoustic frequency in order to distribute the heat in a manner to prevent burning the patient. Since frequency need not be swept, and power need not be minimized, the catheter and its associated equipment can be optimized for operation at a selected acoustic frequency. For example, the shape of acoustic coupling surface 34 of follower 30 can be optimized at the selected frequency to distribute the acoustic energy in a selected manner. Similarly, the larger available power may permit treatment under conditions in which treatment could not be performed in the prior art.

Figure 2:
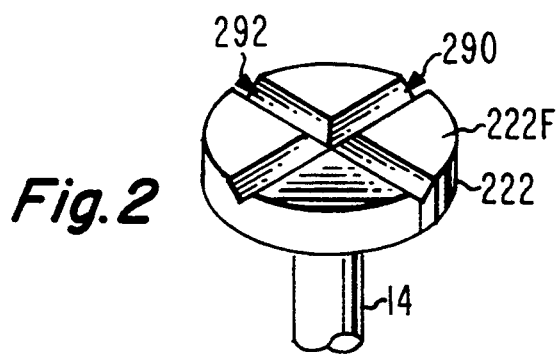
FIG. 2 is a simplified perspective or isometric view of an alternative form of swash plate which may be used in the arrangement of FIG. 1.

FIG. 2 is a representation of a swash plate which may be easier to make than the swash plate of FIG. 1, and which may provide a greater acoustic-frequency for the same shaft rotational rate. In FIG. 2, a swash plate 222 is coaxially coupled to shaft 14. Swash plate 222 has a front surface designated 222F, which is a generally flat, circular surface. During manufacture, front surface 222F is scribed or cut to form a first V-shaped groove 290 extending across its diameter, followed by forming a second groove 292 at right angles to the first. The net result is a surface which, along any peripheral path, or any circular path coaxial with shaft 14, includes four high spots (the uncut regions) and four valleys. Comparison with the arrangement of swash plate 22 of FIG. 1 shows that a follower driven by swash plate 222 will have twice as many excursions for each rotation of the swash plate, and the acoustic frequency, for a 200,000 RPM drive, will be double 6666 Hz, or 13,300 Hz. Similarly, if three grooves were scribed across the front surface of the swash plate at 120° increments, the acoustic frequency would be three times 6666 Hz, or 20 KHz. A mathematical analysis indicates that the harmonic content of the acoustic energy generated by such V-shaped grooves is only a few percent, and these higher harmonics are quickly attenuated. The V-shaped grooves are expected to wear the legs which bear on them more quickly than the sinusoidal waves described in conjunction with FIG. 1, but a catheter for angioplasty applications is a single-use device, and the duration of treatment cannot be protracted.

Figure 3:
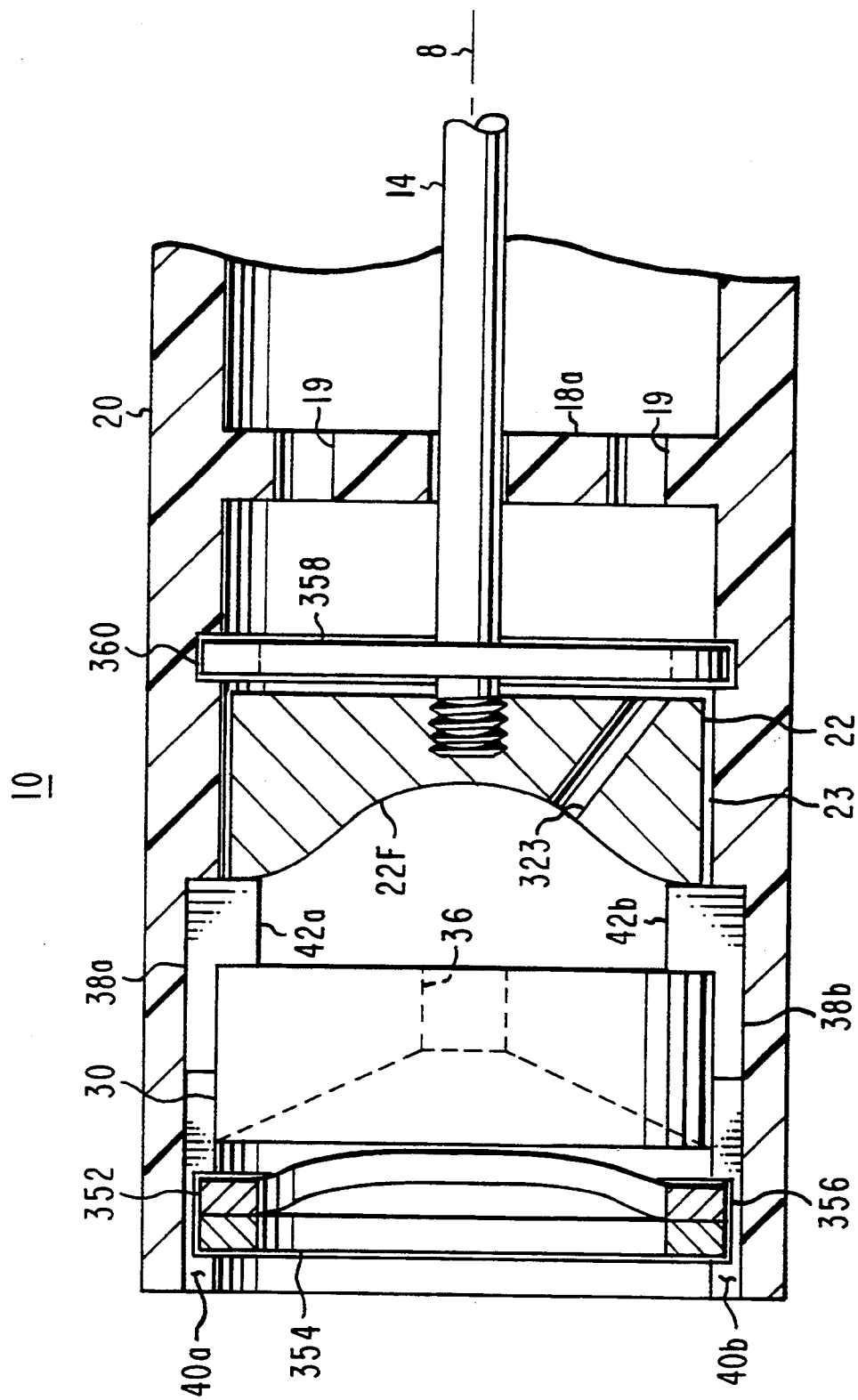
FIG. 3 is a simplified cross-sectional view of the distal end of a catheter similar to that of FIG. 1.

FIG. 3 is a cross-section of the distal end of a catheter according to an embodiment of the invention. The arrangement of FIG. 3 is similar to that of FIG. 1, except that springs 52a and 52b of FIG. 1 are replaced by a spring or Belleville washer 352, which bears against front surface 34 of follower 30, and which is in turn retained by an internal split-ring clip 354 held in a circumferential internal groove 356 inside catheter body 20. Also, another split-ring clip 358 is held in another groove 360 for counteracting the thrust imparted by spring washer 352. Instead of relying on gap or channel 23 to permit aspiration or medication flow past swash plate 22, one or more through channels, one of which is represented as 323, may be defined in swash plate 22.

Figure 4:
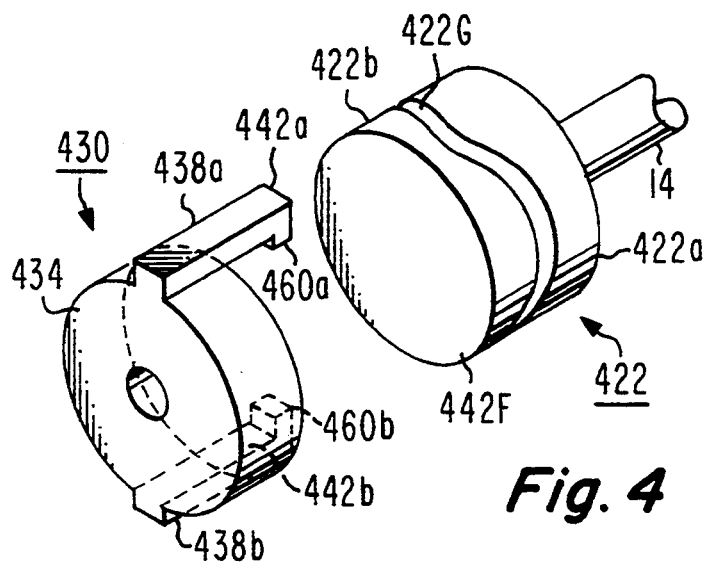
FIG. 4 is a simplified perspective or isometric view of the distal end of a catheter, partially exploded to illustrate the relationships, in which the swash plate and the acoustic head are captivated in a different manner than in FIG. 1.

FIG. 4 represents another form of swash plate 422 and follower 430 which might be used to avoid the need for a spring arrangement. In FIG. 4, the rear of a portion 422a of swash plate 422, 422b is coupled to be driven by shaft 14. A shallow sinusoidal slot or groove 422G separates portions 422a and 422b of swash plate 422. Follower 430 of FIG. 4 includes ribs or ridges 438a and 438b, which fit into corresponding grooves in the catheter body (not illustrated in FIG. 4) for preventing rotation of the follower, and legs 442a and 442b also include protruding tabs 460a and 460b, respectively, which extend past front surface 422F of swash plate 422, and engage with groove 422G. Since ribs or ridges 438a and 438b bear against the inner surface of the catheter body, tabs 460a and 460b are retained in position in the groove. With tabs 460a and 460b engaged in groove 422G, and follower 430 constrained against rotation, the follower is forced to follow the axial motion of the groove. It may be desirable to provide a low-friction connection between the tabs and the groove, such as rollers or TEFLON.

Figure 5:
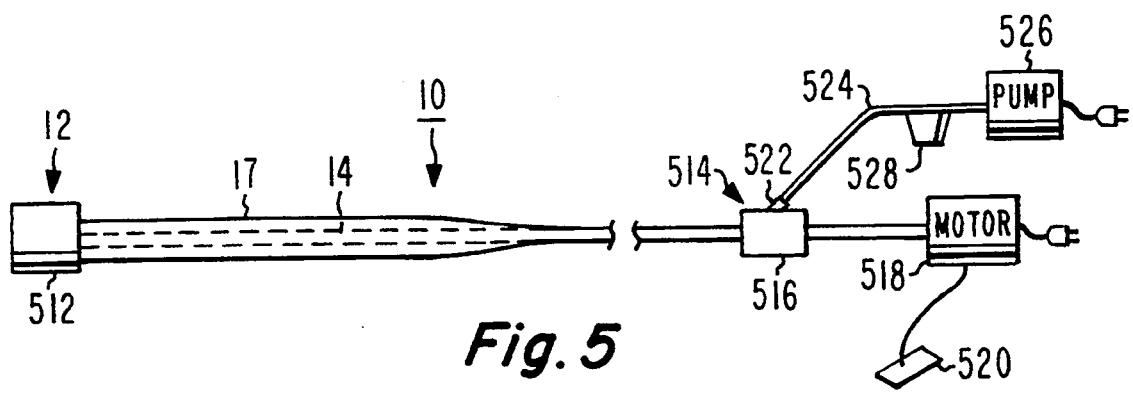
FIG. 5 is a simplified diagram of a catheter according to the invention, connected as required in order to be used with a patient.

FIG. 5 represents a system using a catheter generally as described in conjunction with FIGS. 1, 2, 3 or 4. In FIG. 5, the rotary-to-axial motion or acoustic transducer is located in an enlarged portion 512 at the distal end of catheter 10. Near the proximal end 514 of catheter 10, a junction is represented as a block 516. Block 516 represents an arrangement for connecting a motor and a suction apparatus to catheter 10. As illustrated in FIG. 5, shaft 14 extends from junction 516 and is coupled to a motor 518, which may be turned ON and OFF by means of a foot switch 520, to leave the hands of the surgeon free to manipulate the catheter. A suction tube 524 is connected to a nipple 522 associated with junction 516, for allowing communication with lumen 17. Suction tube 524 is connected to an aspiration pump 526 by way of a fluid container 528.

In operation of the arrangement of FIG. 5, distal end 12 of catheter 10 is introduced into a vas of the body which communicates with the region to be treated, and the distal end is advanced to the treatment region. In the case in which the vas is part of the blood circulatory system, the vas may be an artery, part of which may be atherosclerotic. The distal end 12 of the catheter is advanced to the region with plaque, the aspiration pump 526 is energized, and the foot pedal 520 depressed in order to begin ablation. When depressed, foot pedal 520 causes motor 518 and shaft 14 to rotate, thereby resulting in generation of acoustic energy at the distal end 12 of catheter 10. The acoustic energy loosens or comminutes at least portions of the plaque, which portions are then aspirated. The procedure may be continued until all the plaque is removed, or until the surgeon deems it advisable to end the treatment.

Figure 7:
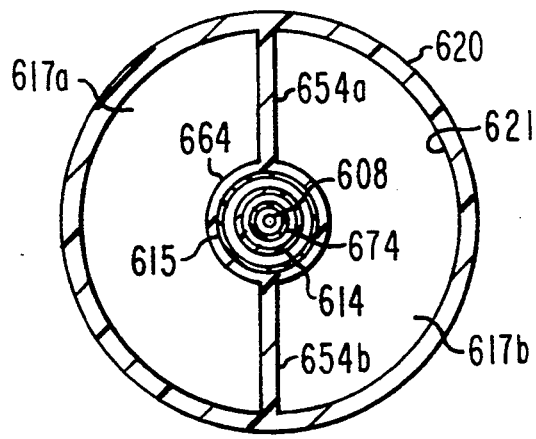
FIG. 7 is a cross-section of the arrangement of FIG. 6, looking in the direction of section lines 7—7.
Figure 6:
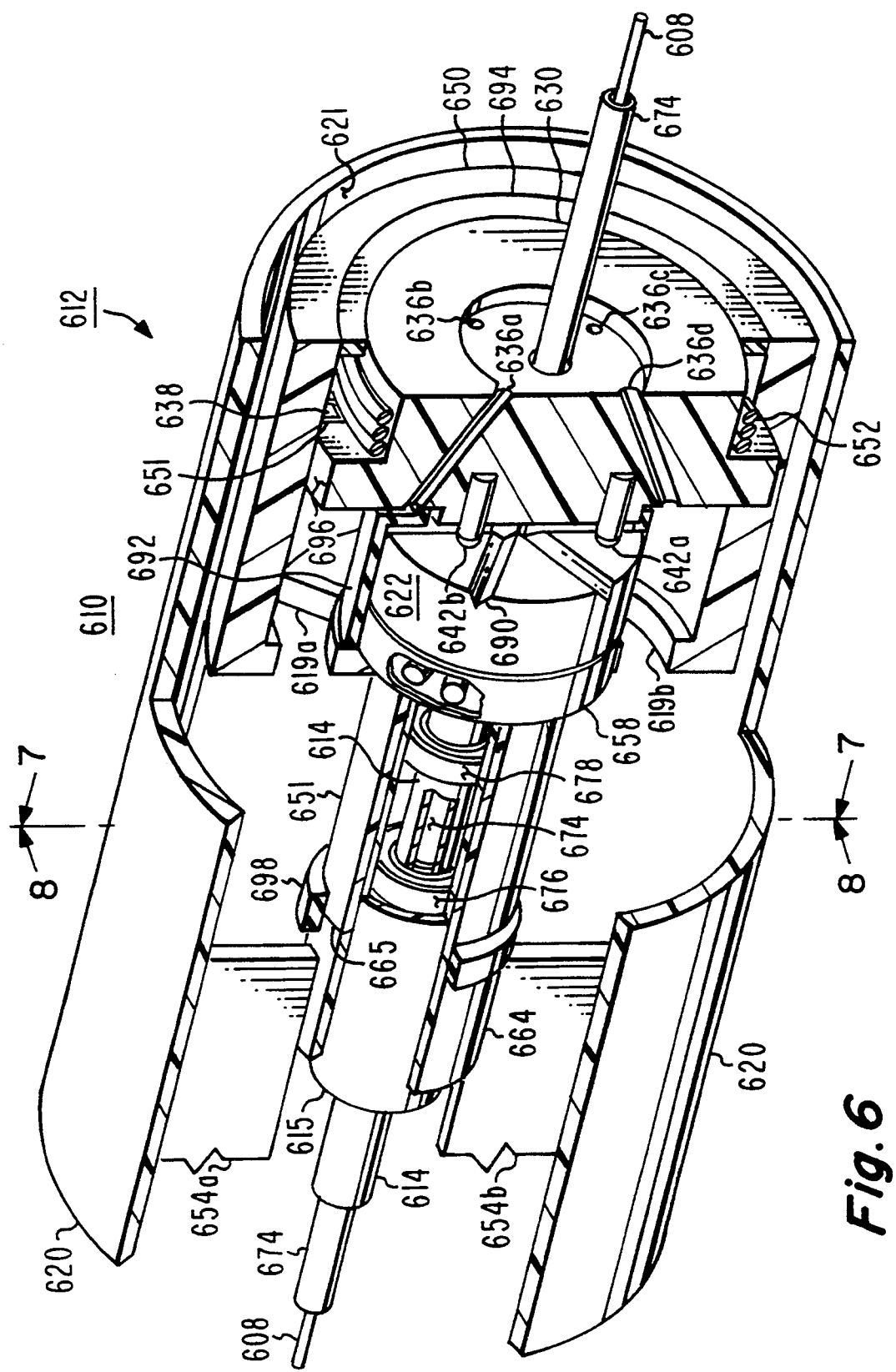
FIG. 6 is a simplified perspective or isometric view of a portion of another embodiment of the invention, in which the rotary shaft is hollow, to allow passage of a guide wire.
Figure 8:
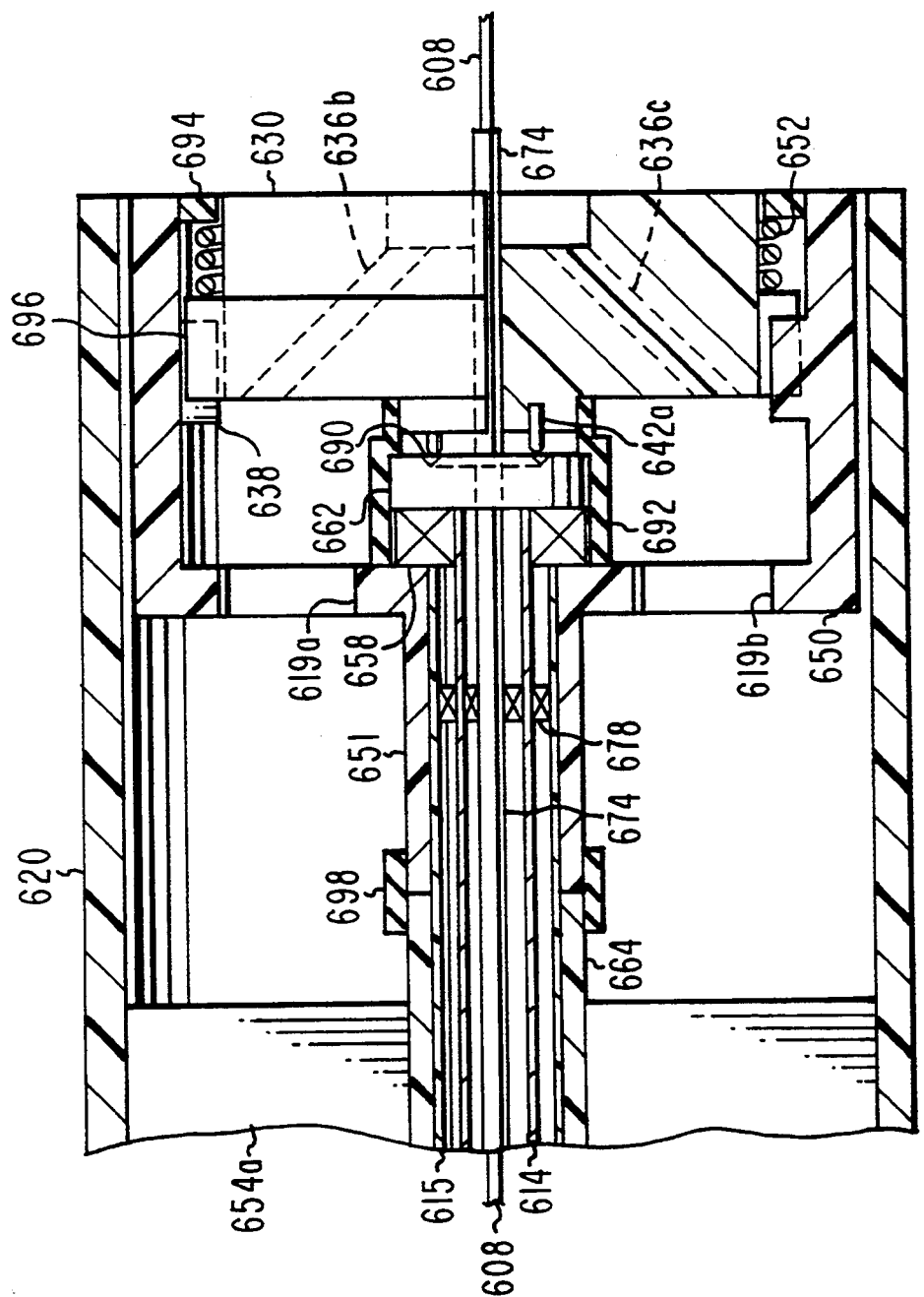
FIG. 8 is a cross-section of the arrangement of FIG. 6, looking in the direction of section lines 8—8.

In FIGS. 6, 7, and 8, distal end 612 of catheter 610 is cut away to show interior details. Catheter 610 of FIG. 6 includes a flexible body 620 defining an interior surface 621, and a pair of flexible septa or septums 654a and 654b, which extend diametrically across the interior of body 620 throughout the length of body 620, and supporting a central lumen housing 664. Since central lumen housing 664 is connected by septa 654a and 654b to outer body 620 of catheter 610, lumen housing 664 does not rotate. A flexible shaft housing 615 fits tightly within central lumen housing 664, and is also immobile. However, hollow shaft 614 is free to rotate within shaft housing 615 on bushings or bearings, two of which are illustrated as 676 and 678. The combination of exterior wall 620, septa 654a and 654b, and central lumen housing 664 defines a pair of longitudinal lumens, illustrated as 617a and 617b, more easily visualized in FIG. 7, which lumens may both be used for aspiration, or which may be used alternately for aspiration and infusion of medicaments by applying differential pressures to the proximal ends of the two lumens. Also in FIG. 6, flexible central lumen housing 664 is coupled at a joint 665 to a rigid extension 651 of a rigid housing 650 by a resilient ring 698, better seen in FIG. 8. An axially movable guide wire 608 lies within a tube 674, which fits within hollow shaft 614.

Swash plate 622 is fixed to shaft 614, and rotates therewith. As illustrated in FIG. 6, three sets of diametric grooves 690 are formed in the distal face of swash plate 622. A set of four follower pins, only two of which, designated 642a and 642b, are visible, couples the front surface of swash plate 622 to acoustic head 630. Acoustic head 630 has a flat front surface, and defines four front-to-back through holes or bores 636a, 636b, 636c, 636d, which allow the flow of fluids through the acoustic head for aspiration or for infusion of medicament. Acoustic head 630 is prevented from rotating under the impetus of the rotation of swash plate 622 by means of a key or boss 638 protruding from the inner surface of stationary rigid housing 650, which engages a keyway 651 formed in a flange 696 of acoustic head 630. Acoustic head 630 is maintained in operational contact with swash plate 622 by a coil spring 652, which is retained in position between flange 696 and an end ring 694, and which urges acoustic head 630 toward swash plate 622. Ring 694 is adhesively fastened to rigid housing 650. Swash plate 622 in turn is urged toward thrust bearing 658. Rigid housing 650 provides a rigid nonrotating base against which thrust bearing 658 may bear. A sealing "O" ring 692 extends from fixed acoustic head 630 to a portion of rigid housing 650, spaced away from rotating swash plate 622, to prevent the flow of fluid around the swash plate, to prevent damping of the desired acoustic vibration.

Figure 9:
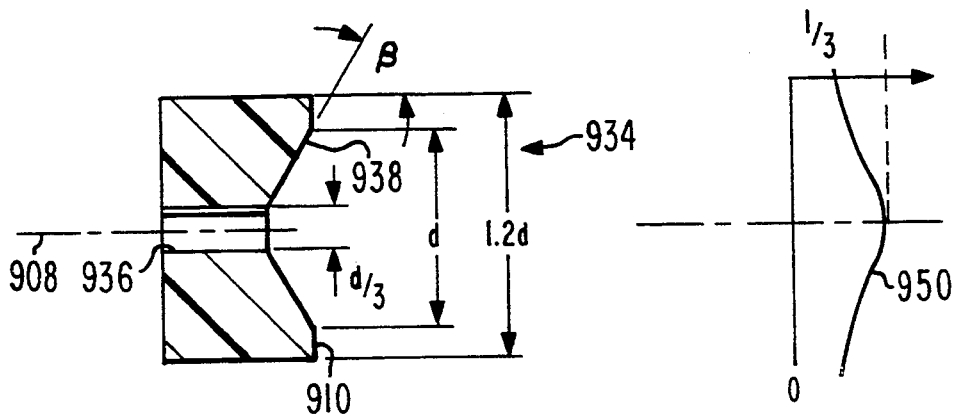
FIG. 9 is a cross-section of an acoustic head according to an aspect of the invention.

FIG. 9 is a cross-sectional representation of an acoustic head. In FIG. 9, the acoustic surface 934 is at the right. As viewed from the patient's side (the side on which the acoustic energy is propagated), surface 934 is concave, and is circularly symmetric about an axis 908. Acoustic surface 934 includes an outer annular ring 910, an aperture 936, and a conical surface 938, all of which are centered on axis 908. It has been found that the angle $\beta$ which conical surface 938 makes with longitudinal axis 908, and the dimensions of annular surface 910, affect the distribution of acoustic energy in the region adjacent the acoustic head. A plot 950 represents the general form of the acoustic energy distribution immediately before the acoustic head. If angle $\beta$ is 90° (a flat front surface), the on-axis energy is only slightly greater than the energy at a distance from the axis equal to the head radius. Thus, there may be a tendency to couple excessive acoustic energy to the walls of a vas or vessel being treated. If angle $\beta$ is very small, the on-axis acoustic energy may be smaller than the energy at one radius from the axis. When the relative dimensions of annular ring 910, aperture 936 and conical surface 938 are as illustrated, and angle $\beta$ is between 60° and 80°, the acoustic energy at a position one radius from the axis is less than about one-half the energy on-axis. As illustrated, the dimensions of the outer diameter of annular surface 910 and the diameter of the central aperture are normalized to the inner diameter of the annular surface; the outer diameter of annular surface 910 should be 1.2 times its inner diameter, and the diameter of central aperture 936 should be about ⅓ that of the inner diameter of annular surface 910.

Other embodiments of the invention will be apparent to those skilled in the art. For example, in order to minimize the forces required to move the follower, it may be made from a low mass, high strength material, such as carbon-fiber reinforced resin. Since the forces required to move the follower itself are minimized by minimizing its mass in this fashion, the restoring force of the spring, and its mass, may also be reduced, thereby reducing the power required to achieve a particular acoustic power, or, without changes to the spring, a higher acoustic frequency can be achieved. While V-shaped grooves have been illustrated in the embodiment of FIG. 2, square-bottom grooves could be used, or any other shape. Instead of cutting V-shaped grooves into a flat front surface of a swash plate, the grooves could be embossed into the surface, in which case any shape peak and valley could be economically manufactured, and the 3× frequency multiplication, or even more, could be achieved with sinusoidal peaks and valleys. The acoustic catheter has been described with only one or two lumens or paths extending therethrough, but those skilled in the art will know that the lumen(s) can be used for other purposes, or that more than two lumens may be provided, if desired, for the flow of medicaments, dyes or sterile solutions to the patient. The described acoustic catheter can include, or be paralleled with, a fiber optic scope, and or with other equipment, as for example an electromagnetic transmission line for application of microwaves, in addition to acoustic energy, to the region to be treated. The rotational motion of the shaft may be used for aiding the flow of fluid through the lumen, by making the swash plate with suitable centrifugal impeller characteristics. Instead of a coil spring such as 652 or a bent washer such as 352 for urging the follower into contact with the swash plate, an elastic "O" ring could be used.

What is claimed is:

1. A catheter for generating acoustic energy in a biological medium when portions thereof are driven by a rotary motor, comprising;
    an elongated body defining a distal end and a proximal end;
    a shaft extending longitudinally through said body, and including drive coupling means near said proximal end of said catheter, adapted to be coupled to said rotary motor for causing said shaft to be driven with a rotary motion; and
    rotary-to-axial motion conversion means coupled to said shaft near said distal end of said catheter, and also coupled to said medium, for converting said rotary motion into reciprocal axial motion in the form of acoustic energy.

2. A catheter according to claim 1, wherein said rotary-to-axial motion conversion means comprises:
    a swash plate coupled to said shaft for being driven in a rotary motion thereby, said swash plate defining a surface which, at a reference point fixed relative to said catheter body, moves axially in response to said rotary motion of said swash plate; and
    follower means coupled to said swash plate and coupled to said surface of said swash plate, for moving axially in response to said axial motion of said surface.

3. A catheter according to claim 2, wherein said follower means comprises:
    a follower body defining a projecting portion bearing on said swash plate; and
    means coupled to said follower body and said catheter body, for causing said follower body to follow said swash plate.

4. A catheter according to claim 3, wherein said means coupled to said follower body and said catheter body for causing said follower body to follow said swash plate comprises spring means bearing on said follower body.

5. A catheter according to claim 2, wherein said swash plate comprises:
    a first surface defining a center, said first surface being coupled to said shaft for being driven thereby, with said center of said first surface lying on the axis of said shaft; and
    a second surface, generally parallel to said first surface, in the shape of a regular figure inscribed about a center point on said second surface which lies on an extension of said axis of said shaft, said second surface also defining at least one notche on a diameter running through said center point, and, when a plurality of said notches are present, said notches being spaced at equal angles about said center point.

6. A catheter according to claim 5, wherein said notches are depressed below said second surface in a direction parallel to said axis of said shaft.

7. A catheter according to claim 2, wherein said follower means includes a distal surface which is concave as seen from a point more distal than the distal end of said catheter, for shaping the distribution of said acoustic energy.

8. A catheter according to claim 2, wherein:
    said catheter defines an open path for the aspiration of fluid from a distal portion of said catheter to a proximal portion of said catheter;
    said open path is coupled at a proximal end thereof to an aspiration connection means, for making a connection of said open path to an aspirator; and
    said follower defines a bore parallel with said axis of said shaft and communicating with said open path, whereby, when said catheter is in operation and material is being loosened by said acoustic energy, the matter so loosened may be aspirated.

9. A method for performing a medical procedure, comprising the steps of:
    inserting into a patient the distal end of a catheter body;
    rotating a shaft extending axially through said catheter body;
    rotating a swash plate coupled to the distal end of said shaft, whereby said swash plate creates reciprocal axial motion relative to said catheter body at a location angularly fixed with respect to said catheter body;
    moving a follower axially relative to said body in response to said axial motion of said swash plate to thereby generate acoustic energy; and
    directing said acoustic energy toward the region in which the medical procedure is to be performed.

10. A method according to claim 9, wherein said step of moving a follower further comprises the step of focussing said acoustic energy.

11. A method according to claim 9, wherein said medical procedure comprises the step of applying said acoustic energy to free unwanted matter; and further comprising the step of:

evacuating at least a portion of said unwanted matter.

12. A method according to claim 11, wherein said step of evacuating includes the step of applying aspirating suction to the proximal end of a lumen extending through said catheter.

* * * * *